(12) United States Patent
Beeckler et al.

(10) Patent No.: US 11,478,609 B2
(45) Date of Patent: Oct. 25, 2022

(54) BENDABLE GUIDEWIRE

(71) Applicant: Biosense Webster (Israel) Ltd., Yokneam (IL)

(72) Inventors: Christopher Thomas Beeckler, Brea, CA (US); Joseph Thomas Keyes, Glendora, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 257 days.

(21) Appl. No.: 16/584,577

(22) Filed: Sep. 26, 2019

(65) Prior Publication Data
US 2021/0093832 A1    Apr. 1, 2021

(51) Int. Cl.
*A61M 25/00* (2006.01)
*A61M 25/09* (2006.01)

(52) U.S. Cl.
CPC .... *A61M 25/0051* (2013.01); *A61M 25/0013* (2013.01); *A61M 25/09* (2013.01); *A61M 2025/09108* (2013.01); *A61M 2025/09116* (2013.01); *A61M 2210/0693* (2013.01); *A61M 2210/12* (2013.01)

(58) Field of Classification Search
CPC .......... A61M 25/0051; A61M 25/0013; A61M 25/09; A61M 2025/09108; A61M 2025/09116; A61M 2210/0693; A61M 2210/12; A61M 25/0138; A61M 2025/0915; A61M 25/0054; A61M 25/09041; A61M 2025/0042; A61B 17/22; A61B 2017/22038; A61B 2017/00309; A61B 2017/00331
See application file for complete search history.

(56) References Cited

U.S. PATENT DOCUMENTS

| 5,957,903 A | 9/1999 | Mirzaee et al. |
| 7,708,704 B2 | 5/2010 | Mitelberg et al. |
| (Continued) | | |

FOREIGN PATENT DOCUMENTS

| EP | 1 656 963 A1 | 5/2006 |
| JP | H08257128 A | 8/1996 |
| (Continued) | | |

OTHER PUBLICATIONS

EP 20198624-1132—Extended European Search Report dated Mar. 9, 2021.

*Primary Examiner* — Brandy S Lee
*Assistant Examiner* — Hong-Van N Trinh
(74) *Attorney, Agent, or Firm* — Troutman Pepper Hamilton Sanders, LLP

(57) ABSTRACT

An apparatus includes a tube configured for insertion into a body of a subject, the tube comprising a plurality of strips, which are angled obliquely with respect to a longitudinal axis of the tube, by virtue of the tube being shaped to define a plurality of slits having respective oblique proximal ends and respective oblique distal ends. The distal end of each of the slits is nested between the proximal end of a first other one of the slits and the proximal end of a second other one of the slits such that (i) one of the strips is disposed between the distal end of the slit and the proximal end of the first other one of the slits, and (ii) another one of the strips is disposed between the distal end of the slit and the proximal end of the second other one of the slits.

20 Claims, 3 Drawing Sheets

(56) References Cited

U.S. PATENT DOCUMENTS

| | | |
|---|---|---|
| 2005/0027287 A1 | 2/2005 | O'Connor et al. |
| 2006/0100571 A1 | 5/2006 | Venturelli |
| 2006/0100687 A1 | 5/2006 | Fahey et al. |
| 2007/0135763 A1* | 6/2007 | Musbach .......... A61M 25/0054 604/96.01 |
| 2011/0130648 A1 | 6/2011 | Beeckler et al. |
| 2016/0100745 A1* | 4/2016 | Seto .................. G02B 23/2476 600/139 |
| 2016/0287054 A1 | 10/2016 | Fujitani |
| 2017/0189104 A9 | 7/2017 | Govari et al. |
| 2018/0015254 A1* | 1/2018 | Cragg ............... A61M 25/0108 |
| 2018/0067824 A1 | 4/2018 | Conti et al. |
| 2018/0093070 A1* | 4/2018 | Cottone ............... A61M 25/09 |
| 2019/0217052 A1 | 7/2019 | Tal et al. |

FOREIGN PATENT DOCUMENTS

| | | |
|---|---|---|
| WO | 2004/047899 A1 | 6/2004 |
| WO | 2012158152 A1 | 11/2012 |
| WO | 2017/191636 A1 | 11/2017 |
| WO | 2018/067824 A1 | 4/2018 |

\* cited by examiner

BENDABLE GUIDEWIRE

FIELD OF THE INVENTION

The present invention is related to the field of medical devices, and particularly to guidewires and catheters for insertion into a body.

BACKGROUND

US Patent Application Publication 2011/0130648 describes a medical probe, consisting of a flexible insertion tube, having a distal end for insertion into a body cavity of a patient, and a distal tip, which is disposed at the distal end of the flexible insertion tube is configured to be brought into contact with tissue in the body cavity. The probe also includes a coupling member, which couples the distal tip to the distal end of the insertion tube and which consists of a tubular piece of an elastic material having a plurality of intertwined helical cuts therethrough along a portion of a length of the piece.

U.S. Pat. No. 7,708,704 describes a component for use as or for incorporation within a medical instrument navigable through body vessels of a human subject. The component includes a tubular portion with an interrupted spiral defined by alternating cut and uncut sections. The sum of the arcuate extents of each bridge section and a cut section adjacent to the bridge section in end-to-end fashion is neither a whole number factor of 360 degrees nor a multiple of 90 degrees. The device further includes multiple sections, the pitch of the spiral varying from section to section in order to vary the sections' flexibilities.

SUMMARY OF THE INVENTION

There is provided, in accordance with some embodiments of the present invention, an apparatus including a tube configured for insertion into a body of a subject. The tube includes a plurality of strips, which are angled obliquely with respect to a longitudinal axis of the tube, by virtue of the tube being shaped to define a plurality of slits having respective oblique proximal ends and respective oblique distal ends. The distal end of each of the slits is nested between the proximal end of a first other one of the slits and the proximal end of a second other one of the slits such that (i) one of the strips is disposed between the distal end of the slit and the proximal end of the first other one of the slits, and (ii) another one of the strips is disposed between the distal end of the slit and the proximal end of the second other one of the slits.

In some embodiments, at least some of the strips are arranged helically along the tube.

In some embodiments, the proximal ends and distal ends of the slits are angled at an angle of between 5 and 85 degrees with respect to the longitudinal axis.

In some embodiments, a density of the slits is greater at a distal portion of the tube than at a proximal portion of the tube.

In some embodiments,
the slits have respective middle portions, the middle portion of each of the slits being perpendicular to the longitudinal axis and running from the proximal end of the slit to the distal end of the slit, and
the tube further includes a plurality of wider strips that are wider than the strips, each of the wider strips being disposed between a successive two of the middle portions.

In some embodiments, a width of each of the strips is between 0.0025 and 0.075 mm.

In some embodiments, an arc length of each of the strips is between 0.3 and 0.9 times an outer diameter of the tube.

In some embodiments, each slit-end of at least some of the proximal ends and some of the distal ends widens toward a termination of the slit-end.

In some embodiments, a bend radius of the tube is less than half an outer diameter of the tube.

In some embodiments, a thickness of a wall of the tube is between 25 and 150 microns.

In some embodiments, an outer diameter of the tube is between 0.012" and 0.04".

In some embodiments, a length of the tube is between 150 and 400 cm.

There is further provided, in accordance with some embodiments of the present invention, a method including forming, in a tube configured for insertion into a body of a subject, a plurality of strips that are angled obliquely with respect to a longitudinal axis of the tube, by forming, in the tube, a plurality of slits having respective oblique proximal ends and respective oblique distal ends. The distal end of each of the slits is nested between the proximal end of a first other one of the slits and the proximal end of a second other one of the slits such that (i) one of the strips is disposed between the distal end of the slit and the proximal end of the first other one of the slits, and (ii) another one of the strips is disposed between the distal end of the slit and the proximal end of the second other one of the slits. The method further includes inserting one or more components into the tube.

The present invention will be more fully understood from the following detailed description of embodiments thereof, taken together with the drawings, in which:

DETAILED DESCRIPTION OF EMBODIMENTS

Overview

Typically, to impart flexibility to a guidewire, a plurality of slits are formed in the outer tube of the guidewire during the manufacture thereof. A challenge, however, is that when the guidewire bends, the bending stress imparted to the remaining uncut portions of the outer tube may cause these uncut portions to crack, due to poor distribution of the stress.

To address this challenge, embodiments of the present invention provide the slits with one or more stress-distributing features, such that the bending stress applied to the guidewire does not cause the outer tube of the guidewire to crack. For example, the ends of the slits (or "slit-ends") may be angled obliquely with respect to the longitudinal axis of the guidewire, and/or each of at least some of the slit-ends may widen toward the termination of the slit-end. Alternatively or additionally, the number of bendable uncut portions of the outer tube may be increased, by nesting the distal end of each slit between the respective proximal ends of two other slits.

In the context of the present application, including the claims, a variable is said to "approximately" attain a particular value if the variable is within ±10% of that value.

Apparatus Description

Figure 1:
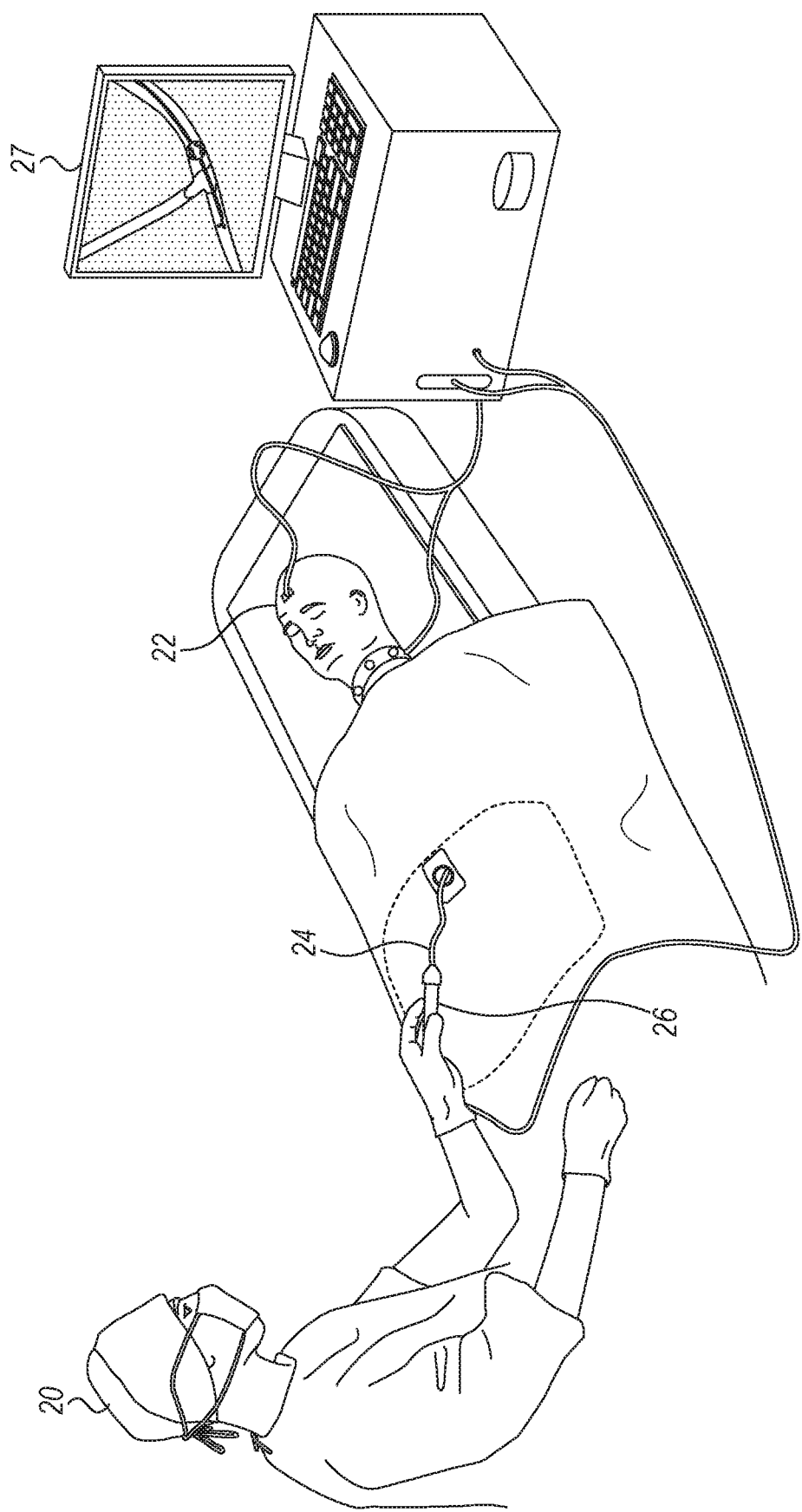
FIG. 1 is a schematic illustration of a surgical procedure, in accordance with some embodiments of the present invention.

Reference is initially made to FIG. 1, which is a schematic illustration of a surgical procedure, in accordance with some embodiments of the present invention.

FIG. 1 depicts a procedure for removal of a clot from a blood vessel, such as a cranial blood vessel, of a subject 22. During this procedure, a physician 20 inserts a guidewire 24 into the body of subject 22, e.g., via an artery in a thigh of the subject. Subsequently, physician 20 navigates the guidewire to the target site at which the clot is located, using a guidewire torquer 26 coupled to the proximal end of guidewire 24. During the procedure, the target site may be displayed on a display 27.

Subsequently to the guidewire reaching the target site, the physician delivers one or more tools over the guidewire, and then uses the tools to perform surgery at the site. For example, the physician may deliver a microcatheter over the guidewire, after which the guidewire may be withdrawn. Next, the physician may insert a stent retriever through the microcatheter, and advance both the microcatheter and the stent retriever into the clot. Subsequently, the physician may withdraw the microcatheter such that the stent retriever expands within the clot, thus opening the blood vessel.

Guidewire 24 comprises an outer tube, which facilitates the navigation of the guidewire by distally transferring the torque applied to the guidewire by the physician. As further described below with reference to FIGS. 2A-B, the outer tube of the guidewire comprises a plurality of bendable strips, which, by bending, facilitate flexion of the outer tube. Advantageously, the bendable strips are configured to distribute the bending stress applied to the outer tube such that the bending stress at any one particular point does not exceed the threshold bending stress at which the outer tube would crack. Thus, the outer tube may bend (or "flex") even at sharp angles. In other words, the bend radius of the outer tube—i.e., the minimum radius at which the outer tube can bend without cracking (or undergoing any other type of damage)—may be relatively small, e.g., equal to or less than half the outer diameter of the tube. By virtue of this flexibility, the guidewire may be navigated even to regions of the brain that are generally hard to reach, such as the M2 region of the middle cerebral artery.

In addition to the aforementioned outer tube, the guidewire may comprise any other suitable components, which may be disposed, for example, within the outer tube. Examples of such components include a coil for reinforcing the outer tube, sensors (e.g., electromagnetic sensors) for use with a position-tracking system, fiber-optical components, and/or wires for carrying electrical signals. These components may be inserted into the outer tube during the manufacture of the guidewire.

Notwithstanding the particular type of procedure shown in FIG. 1, it is noted that guidewire 24 may be used in any suitable procedure. The guidewire may be inserted into any appropriate portion of a body, such as a paranasal sinus, a vena cava, or another blood vessel. Moreover, any suitable medical device may be guided over the guidewire.

Figure 2A:
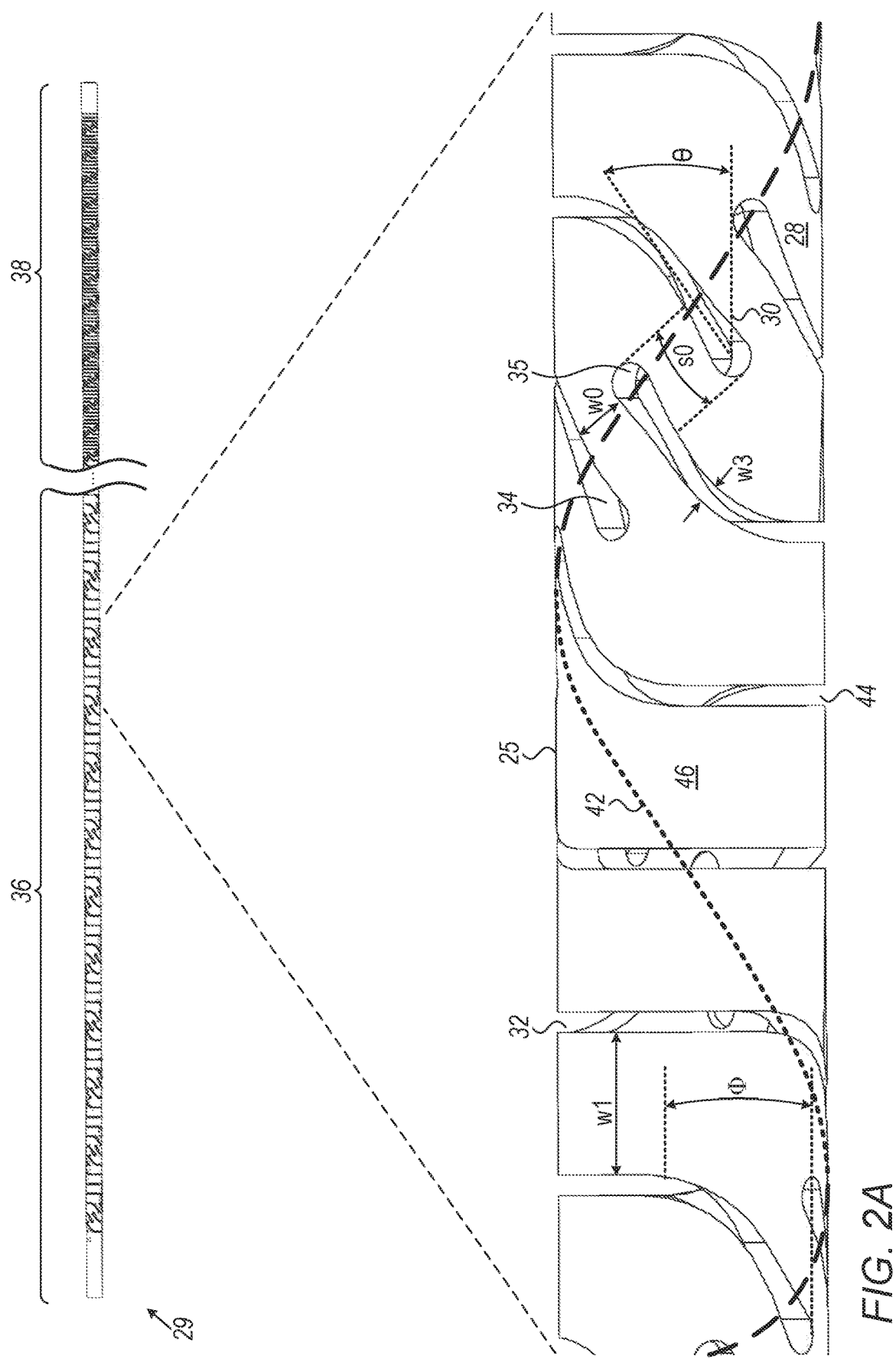
FIGS. 2A-B are schematic illustrations of the outer tube of a guidewire, in accordance with some embodiments of the present invention.
Figure 2B:
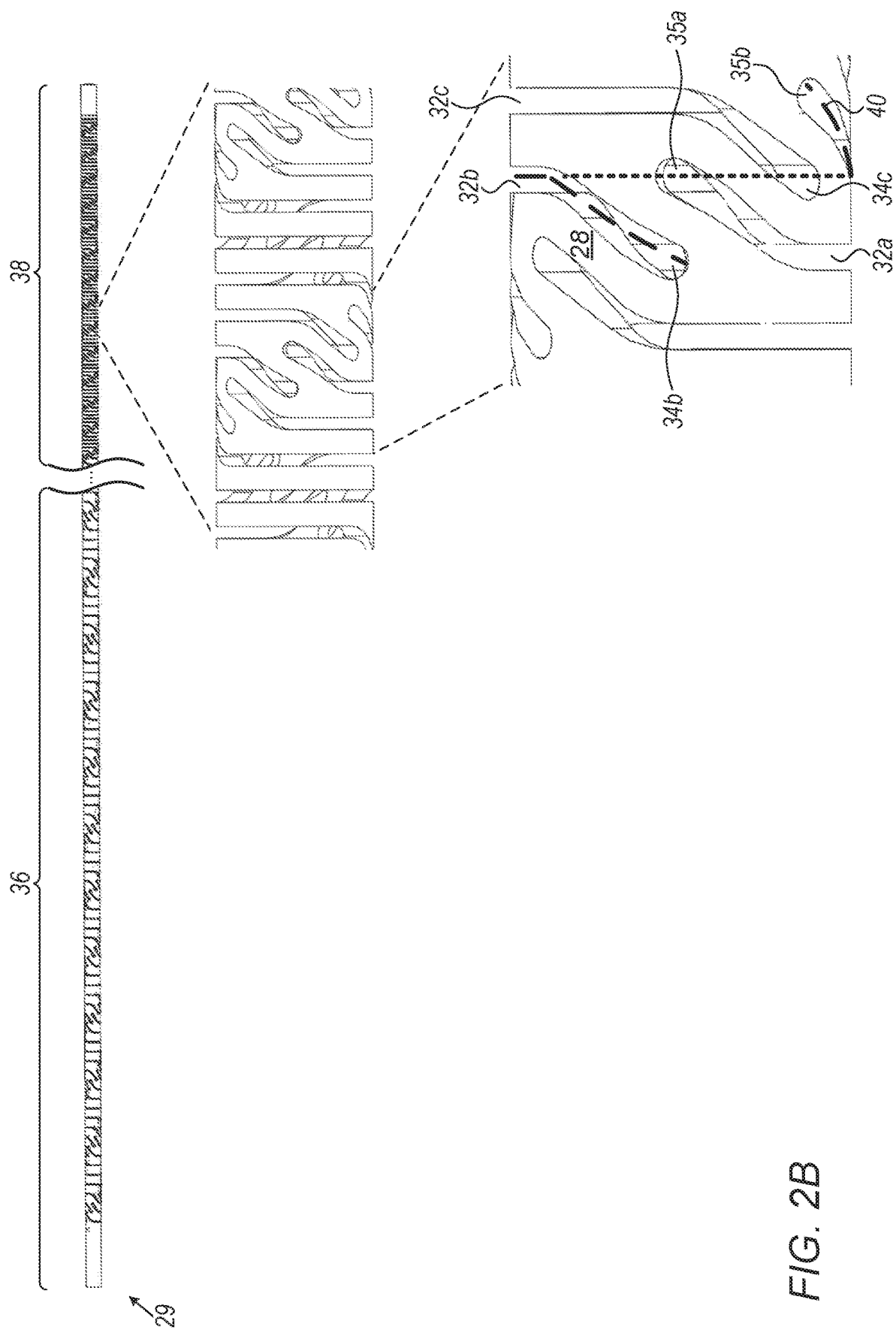

Reference is now made to FIGS. 2A-B, which are schematic illustrations of the outer tube 29 of guidewire 24, in accordance with some embodiments of the present invention. FIG. 2A expands part of the proximal portion 36 of outer tube 29, while FIG. 2B expands part of the distal portion 38 of the outer tube.

Outer tube 29 comprises a cylindrical wall 25 surrounding a lumen, within which other components of the guidewire (e.g., a reinforcing coil) may be disposed, as described above with reference to FIG. 1. Wall 25 may be made of any suitable material, such as a metal (e.g., Nitinol, stainless steel, or titanium) or a polymer. Typically, the thickness of wall 25 is between 25 and 150 microns. Further typically, the length of the tube is between 150 and 400 cm, and/or the outer diameter of the tube is between 0.012" and 0.04".

Outer tube 29 is shaped to define a plurality of slits (or "cuts") 32; in other words, slits 32 are formed in wall 25 of the tube. By virtue of slits 32, the tube comprises a plurality of bendable strips 28; more specifically, as further described below, bendable strips 28 are disposed between the ends of slits 32. The width w0 of each of the bendable strips is relatively small (e.g., between 0.025 and 0.1 mm), such that the bendable strips bend in response to an applied torque. (It is noted that the width of each strip is not necessarily constant along the length of the strip.)

Slits 32 may be formed using any suitable technique, such as laser cutting, electric discharge machining, conventional machining (e.g., milling and/or lathing), or chemical etching. Typically, the density of the slits (i.e., the number of slits per unit length of the tube)—and hence, the flexibility of the tube—increases moving distally along the tube. For example, as shown in FIGS. 2A-B, the tube may comprise two portions: proximal portion 36, along which the density of the slits has a first, lower value, and distal portion 38, along which the density has a second, higher value. The tube may further comprise one or more middle portions, which have respective intermediate slit-density values and are disposed between proximal portion 36 and distal portion 38. For example, the density of the slits may gradually increase (moving distally) over the length of the tube, such that the density attains a continuum of values, e.g., 10 or more discrete values. (In some embodiments, as shown in FIGS. 2A-B, the distal end of the tube, and/or the proximal end of the tube, are not shaped to define any slits.)

Due to the greater density of the slits along distal portion 38, w0 may be less at the distal portion of the tube than at the proximal portion of the tube. As a purely illustrative example, w0 may be approximately 0.0025" at the proximal portion and approximately 0.0015" at the distal portion. For embodiments in which the tube comprises one or more middle portions, w0 may attain any number of intermediate values between the proximal and distal portions of the tube.

To help distribute the bending stress applied to the tube and thus reduce the risk of the tube cracking, the ends of the slits—and hence, the bendable strips of the tube—are angled obliquely with respect to the longitudinal axis 30 of the tube, such that the bendable strips are partially aligned with the bend direction. In other words, each slit has an oblique proximal end 34 and an oblique distal end 35, in that the angle $\theta$ between each of the slit-ends and longitudinal axis 30 is greater than zero and less than 90 degrees. For example, $\theta$ may be between 5 and 85 degrees.

Due to the greater density of the slits along distal portion 38, angle $\theta$ may be greater at distal portion 38 than at proximal portion 36. For example, angle $\theta$ may be between 10 and 40 degrees at the proximal portion of the tube, and between 30 and 60 degrees at the distal portion of the tube. For embodiments in which the tube comprises one or more middle portions, $\theta$ may attain any number of intermediate values between the proximal and distal portions of the tube.

In some embodiments, to facilitate an increased number of slits—and hence, an increased number of bendable strips—in tube 29, distal end 35 of each of the slits (except for the distalmost two slits) is situated (or "nested") between the proximal end of a first other slit and the proximal end of a second other slit. By virtue of this nesting, one bendable strip is disposed between the distal end of the slit and the proximal end of the first other slit, and another bendable strip is disposed between the distal end of the slit and the proximal end of the second other slit. (Equivalently, it may be said that the proximal end of each of the slits, except for the proximalmost two slits, is nested between the respective distal ends of two other slits, such that two bendable strips are disposed proximally and distally, respectively, to the proximal end.)

For example, FIG. 2B shows a first slit 32a having a distal end 35a nested between (i) the proximal end 34b of a first other slit 32b, and (ii) the proximal end 34c of a second other slit 32c. Likewise, the distal end 35b of slit 32b is nested between proximal end 34c and the proximal end of yet another slit. (For clarity, a curve 40 traces the path of slit 32b, the dotted portion of curve 40 corresponding to the portion of the slit running along the far side of the tube.)

Typically, at least some of the bendable strips are arranged helically along the tube, i.e., a hypothetical helical curve 42 (FIG. 2A) running along the tube passes through the bendable strips. Advantageously, by virtue of this arrangement, the tube does not have a preferential direction of flexion.

Typically, the angular length of each slit (i.e., the angle along the circumference of the outer tube spanned by the slit) is between 200 and 480 degrees. For example, as shown in FIGS. 2A-B, the angular length of each slit may be approximately 270 degrees.

In some embodiments, slits 32 have respective middle portions 44, middle portion 44 of each slit being perpendicular to longitudinal axis 30 and running from the proximal end of the slit to the distal end of the slit. In other embodiments, slits 32 do not have middle portions 44; rather, the slits are entirely oblique.

Typically, the angular length $\phi$ of each slit-end is between 20 and 240 degrees. Since $\phi$ is typically the same for the proximal and distal slit-ends, $\phi$ is typically $(\beta-\gamma)/2$, where (i) $\beta$ is the angular length of the slit, and (ii) $\gamma$ is the angular length of middle portion 44, or zero if the slit does not comprise a middle portion. ($\beta$ and $\gamma$ are not explicitly marked in FIGS. 2A-B.)

Due to the greater density of the slits along distal portion 38, $\phi$ may be less at the distal portion of the tube than at the proximal portion of the tube. For example, $\phi$ may be 80-100 degrees at the proximal portion of the tube but only 50-70 degrees at the distal portion of the tube. Alternatively, for example, $\phi$ may be 400-480 degrees at the proximal portion of the tube but only 180-320 degrees at the distal portion of the tube. For embodiments in which the tube comprises one or more middle portions, $\phi$ may attain any number of intermediate values between the proximal and distal portions of the tube.

Typically, the arc length s0 of each bendable strip is between 0.3 and 0.9 times the outer diameter of the tube. Thus, for example, for an outer diameter between 0.012" and 0.04", s0 may be between 0.0036" and 0.036". s0 may be less at the distal portion of the tube than at the proximal portion of the tube, as described above for $\phi$.

For embodiments in which slits 32 have middle portions 44, the tube comprises a plurality of wider strips 46, each wider strip 46 being disposed between a successive two of middle portions 44. Wider strips 46 are wider than the bendable strips and hence, typically, do not bend as much as do the bendable strips. Due to the greater density of the slits along distal portion 38, the width w1 of each wider strip may be less at the distal portion 38 than at proximal portion 36. For example, w1 may be approximately 0.007" at the proximal portion and approximately 0.002" at the distal portion. For embodiments in which the tube comprises one or more middle portions, w1 may attain any number of intermediate values between the proximal and distal portions of the tube.

Typically, the width w3 of each slit is between 12 and 75 microns. In some embodiments, width w3 is non-constant for at least some of the slit-ends. For example, each slit-end of at least some of proximal ends 34 and some of distal ends 35 may widen toward the termination of the slit-end, such that the termination of the slit-end is bulbous. Advantageously, the bulbous shape of the slit-ends helps to distribute the stress applied to the slit-ends. In some embodiments, the variation in width w3 along each slit-end is greater at the proximal portion of the tube, where the density of the slits is smaller, than at the distal portion of the tube.

It is noted that the scope of the present invention includes the formation of slits and bendable portions as described herein in any tubular body, including, for example, a catheter or a plumbing snake.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
  a tube configured for insertion into a body of a subject, the tube comprising a plurality of strips, which are angled obliquely with respect to a longitudinal axis of the tube, by virtue of the tube being shaped to define a plurality of slits having respective oblique proximal ends and respective oblique distal ends,
  the distal end of each of the slits being nested between the proximal end of a first other one of the slits and the proximal end of a second other one of the slits such that (i) one of the strips is disposed between the distal end of the slit and the proximal end of the first other one of the slits, and (ii) another one of the strips is disposed between the distal end of the slit and the proximal end of the second other one of the slits, and
  wherein the slits have respective middle portions, the middle portion of each of the slits have a length extending from the oblique proximal end to the oblique distal end, the middle portion of each of the slits being perpendicular to the longitudinal axis along the entire length of the middle portion.

2. The apparatus according to claim 1, wherein at least some of the strips are arranged helically along the tube.

3. The apparatus according to claim 1, wherein the proximal ends and distal ends of the slits are angled at an angle of between 5 and 85 degrees with respect to the longitudinal axis.

4. The apparatus according to claim 1, wherein a density of the slits is greater at a distal portion of the tube than at a proximal portion of the tube.

5. The apparatus according to claim 1,
wherein the tube further comprises a plurality of wider strips that are wider than the strips, each of the wider strips being disposed between a successive two of the middle portions.

6. The apparatus according to claim 1, wherein a width of each of the strips is between 0.0025 and 0.075 mm.

7. The apparatus according to claim 1, wherein an arc length of each of the strips is between 0.3 and 0.9 times an outer diameter of the tube.

8. The apparatus according to claim 1, wherein each slit-end of at least some of the proximal ends and some of the distal ends widens toward a termination of the slit-end.

9. The apparatus according to claim 1, wherein a bend radius of the tube is less than half an outer diameter of the tube.

10. The apparatus according to claim 1, wherein a thickness of a wall of the tube is between 25 and 150 microns.

11. The apparatus according to claim 1, wherein an outer diameter of the tube is between 0.012" and 0.04".

12. The apparatus according to claim 1, wherein a length of the tube is between 150 and 400 cm.

13. A method, comprising:
forming, in a tube configured for insertion into a body of a subject, a plurality of strips that are angled obliquely with respect to a longitudinal axis of the tube, by forming, in the tube, a plurality of slits having respective middle portions, respective oblique proximal ends, and respective oblique distal ends, the middle portion of each of the slits have a length extending from the oblique proximal end to the oblique distal end, the middle portion of each of the slits being perpendicular to the longitudinal axis along the entire length of the middle portion,
the distal end of each of the slits being nested between the proximal end of a first other one of the slits and the proximal end of a second other one of the slits such that (i) one of the strips is disposed between the distal end of the slit and the proximal end of the first other one of the slits, and (ii) another one of the strips is disposed between the distal end of the slit and the proximal end of the second other one of the slits; and
inserting one or more components into the tube.

14. The method according to claim 13, wherein forming the strips comprises forming the strips such that at least some of the strips are arranged helically along the tube.

15. The method according to claim 13, wherein forming the strips comprises forming the strips such that the proximal ends and distal ends of the slits are angled at an angle of between 5 and 85 degrees with respect to the longitudinal axis.

16. The method according to claim 13, wherein forming the slits comprises forming the slits such that a density of the slits is greater at a distal portion of the tube than at a proximal portion of the tube.

17. The method according to claim 13, wherein forming the slits comprises forming the slits such that the tube further includes a plurality of wider strips that are wider than the strips, each of the wider strips being disposed between a successive two of the middle portions.

18. The method according to claim 13, wherein a width of each of the strips is between 0.0025 and 0.075 mm.

19. The method according to claim 13, wherein an arc length of each of the strips is between 0.3 and 0.9 times an outer diameter of the tube.

20. The method according to claim 13, wherein forming the slits comprises forming the slits such that each slit-end of at least some of the proximal ends and some of the distal ends widens toward a termination of the slit-end.

* * * * *